(12) United States Patent
Bazan et al.

(10) Patent No.: US 7,232,913 B2
(45) Date of Patent: Jun. 19, 2007

(54) PARACYCLOPHANE MOLECULES FOR TWO-PHOTON ABSORPTION APPLICATIONS

(75) Inventors: Guillermo C. Bazan, Santa Barbara, CA (US); Bernhard Koehler, Seligenstadt (DE); Hadjar Benmansour, Hyeíg (FR); Janice W. Hong, Santa Barbara, CA (US); Han Young Woo, Goleta, CA (US); Alexander Mikhailovsky, Ventura, CA (US); Hideki Gorohmaru, Yokohama (JP); Shuuichi Maeda, Yokohama (JP); T. Kojima, Yokohama (JP); Motoyuki Shigeiwa, Yokohama (JP)

(73) Assignee: The Regents of the University of California, Oakland, CA (US)

( * ) Notice: Subject to any disclaimer, the term of this patent is extended or adjusted under 35 U.S.C. 154(b) by 185 days.

(21) Appl. No.: 10/952,624

(22) Filed: Sep. 28, 2004

(65) Prior Publication Data

US 2006/0208235 A1    Sep. 21, 2006

(51) Int. Cl.
C07D 209/94  (2006.01)
C07D 209/82  (2006.01)
C07C 211/64  (2006.01)
C07C 211/54  (2006.01)
G02B 5/02    (2006.01)
G02F 1/361   (2006.01)

(52) U.S. Cl. .................. 548/439; 548/444; 252/582; 564/434; 564/282

(58) Field of Classification Search ................ 548/439, 548/444; 564/434, 282; 252/582
See application file for complete search history.

(56) References Cited

OTHER PUBLICATIONS

J.AM. Chem.Soc., Bartholomew et al. 2002, vol. 124, 5183-5196.*

Moon, K. -J.; Shim, H. -K.; Lee, K. -S.; Zieba, J.; Prasad, P. N. *Macromolcules* 1996, 29, 861.

Lee, H. J.; Sohn, J.; Hwang, J.; Park, S. Y.; Choi, H.; Cha, M. *Chem. Mater.* 2004, 16, 456.

C.; Webb, W. W. *J. Opt. Soc. Am. B* 1996, 13, 481.

Greenham, N. C.; Samuel, I. D. W.; Hayes, G. R.; Phillips, R. T.; Kessener, Y. A. R. R.; Moratti, S. C.; Homes, A. B.; Friend, R. H. *Chem. Phys. Lett.* 1995, 241, 89.

Bartholomew, G.P.; Rumi, M.; Pond, S.J.K.; Perry, J.W.; Tretiak, S.; Bazan, G.C.; *JACS Articles*, "Two-Photon Absorption in Three-Dimensional Chromophores Based on [2.2]-Paracyclophane"; J.Am. Chem. Soc. xxxx,xxx.

Zyss, J.; Ledoux, I.; Volkov, S.; Chernyak, V.; Mukamel, s.; Bartholomew, G.P. and Bazan, G.C.; *J. American Chemical Society* 2000, vol. 122; "Through-Space Charge Transfer and Nonlinear Optical Properties of Substituted Paracyclophane"; pp. 11956-11962; Published on web Nov. 11, 1990.

Bartholomew, G.P.; Ledoux, I.; Mukamel, S.; Bazan, G.C.; Zyss, J.; *JACS Articles*,; "Three-Dimensional Nonlinear Optical Chromophores Based on Through-Space Delocalization"; vol. 124, pp. 13480-13485, 2002.

Bartholomew, G.P. and Bazan, G.C.; *Accounts of Chemical Research*; vol. 34; "Bichromophoric Paracyclophanes: Models for Interchromphore Delocalization"; No. 1, 2001, pp. 30-39.

* cited by examiner

*Primary Examiner*—Kamal A. Saeed
*Assistant Examiner*—Yong Chu
(74) *Attorney, Agent, or Firm*—Berliner & Associates

(57) ABSTRACT

Chromophores having two-photon or other multi-photon absorptivity. The chromophores are based on a structure of four stilbenoid groups attached to a paracyclophane core, where each stilbenoid group comprises a nitrogen-containing organic group attached by its nitrogen atom to a stilbenoid arm. In particular embodiments, at least one of the stilbenoid groups includes a sulfonium, ammonium, selenium, iodonium or phosphonium moiety. The chromophores have utility as photo-polymerization initiators and two-photon fluorophores for biological imaging.

17 Claims, 1 Drawing Sheet

PARACYCLOPHANE MOLECULES FOR TWO-PHOTON ABSORPTION APPLICATIONS

BACKGROUND

1. Field of Invention

This invention relates generally to chromophores having two-photon or other multi-photon absorptivity.

2. Related Art

Organic molecules that absorb two or more photons simultaneously have wide application in a variety of technologies involving such subjects as optical data storage, 3-D microfabrication techniques, frequency upconverted lasing, optical power limiting, photodynamic therapy, initiators of polymerization reactions, and multi-photon fluorescence microscopy for biological imaging. Two features of the two-photon absorption process make these applications feasible. The first is the quadratic dependence of two-photon absorption on the intensity of the incident radiation. This allows for three dimensional spatial resolution. The second feature is the absence of single-photon absorption, which allows an incident light beam to penetrate deeper into a material than would be possible with single-photon approaches.

Two-photon or other multi-photon absorbing molecules have been designed based on conjugated pi-electron systems with donating groups at each end of the pi-electron system providing charge-transfer properties. For example, U.S. Pat. Nos. 6,267,913 and 6,608,228, both incorporated by reference herein, describe two-photon absorbing chromophores having electron donors such as amino or alkoxy groups attached to a bridge of pi-conjugated bonds. The absorption of two or more photons by such molecules can trigger chemical and physical changes that make these substances useful for two-photon applications. As an example, in photo-polymerization reactions, two-photon absorption by a chromophore leads to the production of reactive starting species such as free radicals, cations or anions that initiate the polymerization process.

SUMMARY

In one aspect, the present invention is directed to two-photon or other multi-photon absorbing chromophores having a conjugated pi-electron system, with donating groups at each end of the pi-electron system providing charge-transfer properties. The chromophores are based on a structure of four stilbenoid groups connected to a paracyclophane core.

More particularly, the present invention is directed to two-photon or other multi-photon absorbing chromophores of formula (I), where $Z^1$, $Z^2$, $Z^3$ and $Z^4$ are stilbenoid arms and $D^1$, $D^2$, $D^3$ and $D^4$ are organic groups, each containing a nitrogen atom connecting the D group to its respective stilbenoid arm.

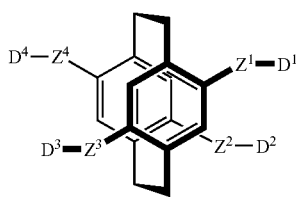

In formula (I), $D^1$, $D^2$, $D^3$ and $D^4$ can be the same or different, and each independently can be a nitrogen-containing group of formula (II) or formula (III).

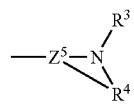

The $R^1$ and $R^2$ groups of formula (II) are each independently hydrogen or a substituted or non-substituted alkyl or aryl group. Alternatively, $R^1$ and $R^2$ taken together with the nitrogen to which they are attached form a substituted or non-substituted, aliphatic or aromatic heterocyclic group.

In formula (III), $Z^5$ is a stilbenoid group, $R^3$ is hydrogen or a substituted or non-substituted alkyl or aryl group, and $R^4$ and N are respectively attached to two carbon atoms of $Z^5$ to form a substituted or non-substituted, aliphatic or aromatic heterocyclic group. $Z^5$ is represented by formula (IV), where $Ar^1$ is a substituted or non-substituted cyclic aromatic group providing the two carbon atoms to which $R^4$ and N are respectively attached.

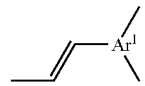

In formula (I), $Z^1$, $Z^2$, $Z^3$ and $Z^4$ are each independently a substituted or non-substituted stilbenoid group of formula (V) wherein $Ar^2$ is an arylene group, and n is an integer from 1 to 5 for a nitrogen-containing group of formula (II), or n is an integer from 0 to 4 for a nitrogen-containing group of formula (III).

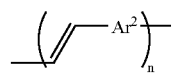

Each of $Z^1$, $Z^2$, $Z^3$, $Z^4$, $Z^5$, $R^1$, $R^2$, $R^3$, and $R^4$ can be independently substitututed one or more halogen, alkyl, aryl, alkoxy, aryloxy, cyano, nitro, aroyl, acyl or hydroxy groups.

The present invention is further directed to compositions, methods of preparation, and methods of use, all incorporating chromophores of the present invention.

DETAILED DESCRIPTION

Figure 1:
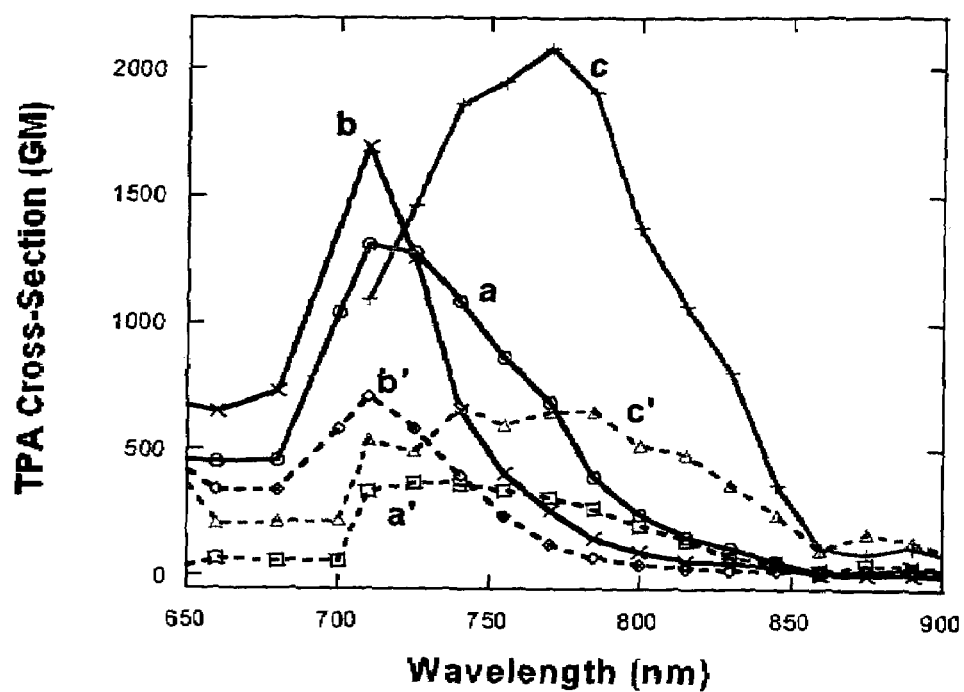
FIG. 1 is a graph showing two-photon absorption spectra of chromophores in toluene or water.

In formula (II), the heterocyclic group formed by $R^1$, $R^2$ and the nitrogen to which they are attached is preferably a 3-8 membered ring. In formula (III), the heterocylic group formed by $R^4$, N and the two carbon atoms of $Z^5$ is preferably a 4-8 membered ring.

Each of $Z^1$, $Z^2$, $Z^3$, $Z^4$, $Z^5$, $R^1$, $R^2$, $R^3$, and $R^4$ can be substituted with one or such groups as:

a) a linear or branched alkyl group of up to 25 carbon atoms such as methyl, ethyl, propyl, butyl, sec-butyl, tert-butyl, pentyl, hexyl, heptyl, octyl, stearyl, 1-methylpentyl, 5-methylhexyl, and 2-phenylisopropyl;

b) $(CH_2CH_2O)_\alpha$—$(CH_2)_\beta CO_2R_{a1}$; —$(CH_2CH_2O)_\alpha$—$(CH_2)_\beta OR_{a2}$; —$(CH_2CH_2O)_\alpha$—$(CH_2)_\beta NR_{a3}R_{a4}$; —$(CH_2CH_2O)_\alpha$—$(CH_2)_{62}$ $CONR_{a3}R_{a4}$; —$(CH_2CH_2O)_{60}$—$(CH_2)_\beta CN$; —$(CH_2CH_2O)_\alpha$—$(CH_2)_\beta Cl$; —$(CH_2CH_2O)_\alpha$—$(CH_2)_{62}$ Br; —$(CH_2CH_2O)_\alpha$—$(CH_2)_\beta I$; —$(CH_2CH_2O)_\alpha$—$(CH_2)_\beta$-Phenyl; where $R_{a1}$, $R_{a2}$, $R_{a3}$, and $R_{a4}$ are each independently H, or a linear or branched alkyl group with up to 25 carbon atoms, and α is 0-10 and β is 1-25;

c) an aryl group such as aromatic hydrocarbons containing up to 20 carbon atoms including phenyl, naphthyl, furanyl, thiophenyl, pyrrolyl, selenophenyl and tellurophenyl;

d) fused aromatic rings such as naphthalene and anthracene; and e) $NR_\alpha R_\beta$; $OR_\gamma$; CHO; CN; $NO_2$; Br; Cl; I; phenyl; where $R_\alpha$, $R_\beta$ and $R_\gamma$ are each independently H or compounds such as those in a), b), c) and d) above.

The chromophores of the present invention can be neutral or ionic compounds. In neutral embodiments where all of the D groups are nitrogen-containing groups of formula (II) and $R^1$ and $R^2$ are each independently hydrogen or a substituted or non-substituted alkyl or aryl group, the neutral embodiments do not include chromophores where all of the $R^1$ and $R^2$ groups of the chromophore (eight R groups total) are simultaneously non-substituted alky groups. Preferably, none of the $R^1$ and $R^2$ groups of the neutral chromophore are non-substituted alkyl groups. More preferably, the $R^1$ and $R^2$ groups of the neutral chromophore are each independently hydrogen or an aryl group.

In preferred neutral embodiments, each of $R^1$, $R^2$ and $R^3$ is independently substituted with one or more halogen groups. For neutral embodiments where each D group is a nitrogen-containing group of formula (II) and $R^1$ and $R^2$ are each independently hydrogen or a substituted or non-substituted alkyl or aryl group, preferred embodiments include chromophores in which all of the $R^1$ and $R^2$ groups of the chromophore (eight groups total) are the same or different substituted alky groups, or the same or different substituted or non-substituted aryl groups.

Preferred neutral embodiments of formula (III) include those in which $D^1$, $D^2$, $D^3$ and $D^4$ are the same or different, where $Ar^1$ is a benzene group, $R^3$ is an alkyl group, and $R^4$ and N taken together with the carbon atoms of $Ar^1$ to which $R^4$ and N are attached form an aromatic heterocycle.

Examples of heterocyclic nitrogen-containing D groups of formula (II) include the following groups.

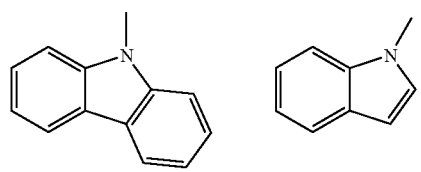

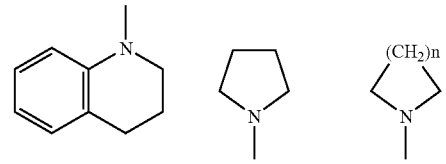

-continued

Examples of nitrogen-containing D group of formula (III) include the following groups.

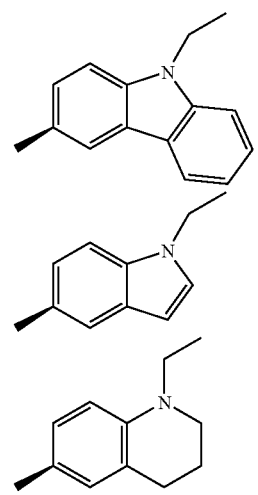

In ionic versions of the chromophores, at least one of $D^1$, $D^2$, $D^3$ and $D^4$ is substituted on $R^1$, $R^2$, $R^3$ or $R^4$ with a sulfonium, ammonium, selenium, iodonium or phosphonium group of respective formula —$S^+X^1X^2$, —$N^+X^1X^2X^3$, —$Se^+X^1X^2$, —$I^{30}$ $X^1X^2$ and —$P^+X^1X^2X^3$, where $X^1$, $X^2$ and $X^3$ are each independently a substituted or non-substituted alkyl or aryl group, and each of $X^1$, $X^2$ and $X^3$ can be independently substituted with one or more halogen, alkyl, aryl, alkoxy, aryloxy, cyano, nitro, aroyl, acyl or hydroxy groups. Chromophores where at least one of the D groups is substituted with a sulfonium or iodonium group are preferred Other preferred embodiments of the ionic chromophores are water-soluble compounds having at least four of eight R groups substituted with ammonium groups, or with phosphonium groups. In further preferred embodiments, all eight R groups of the chromophore are substituted with ammonium groups, or with phosphonium groups.

Additional preferred versions of the ionic chromophores, where each D group is a nitrogen-containing group of formula (II) and $R^1$ and $R^2$ are each independently hydrogen or a substituted or non-substituted alkyl or aryl group, are those embodiments in which all of the $R^1$ and $R^2$ groups of the chromophore (eight groups total) are the same or different substituted alky groups, or are the same or different substituted or non-substituted aryl groups. Preferred ionic versions of formula (III) include those in which $D^1$, $D^2$, $D^3$ and $D^4$ are the same or different, where $Ar^1$ is a benzene group, $R^3$ is an alkyl group, and $R^4$ and N taken together with the carbon atoms of $Ar^1$ to which $R^4$ and N are attached form an aromatic heterocycle.

Ionic chromophores can be represented by general formula (VI) where Y is an anion selected from the group consisting of F⁻, Cl⁻, Br⁻, I⁻, CN⁻, SO₄²⁻, PO₄³⁻, CH₃CO₂⁻, CF₃SO₃⁻, BF₄⁻, PF₆⁻, SbF₆⁻, AsF₆⁻, SbCl₄⁻, ClO₃⁻, ClO₄⁻, NO₂⁻, NO₃⁻ and B(aryl)₄⁻; p is an integer equal to the cationic charge of the chromophore portion of the compound; q is an integer equal to the charge on the anion; and Q and P are integers that satisfy the relationship qQ=pP.

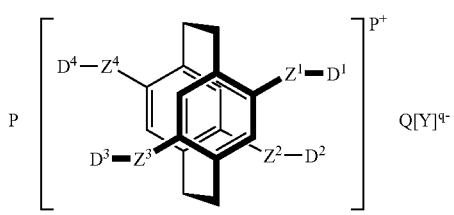

The present invention also provides photo-polymerizeable compositions and a method of photo-polymerization, each incorporating chromophores of the present invention. The method involves mixing a monomer with a two-photon or multi-photon absorbing chromophore of the present invention, and illuminating the mixture. A monomer capable of rapid cationic polymerization can be used with an ionic chromophore of the present invention. Preferred monomers are those containing at least one epoxide group, such as allyl glycidyl ether, aryl glycidyl ether, neopentyl glycol diglycidyl ether, bis(3,4-epoxycyclohexylmethyl)adipate, diglycidyl o-phthalate, and sorbitol polyglycidyl ether. In addition, acrylate monomers capable of radical photo-polymerization can be used with a neutral chromophore of the present invention. Preferred monomers include methylacrylate, methylmethacrylate, and various tri- and penta-acrylates.

The following examples will illustrate the invention. Examples 1-5 describe the synthesis and characterization of an ionic chromophore. Prospective Example 6 describes the use of the ionic chromophore as a polymerization initiator, and Prospective Examples 7-12 describe other ionic chromophores. Examples 13-18 describe the synthesis and characterization of neutral and water soluble ionic chromophores. Prospective Example 19 describes the use of the neutral chromophores as photo-polymerization initiators, and Prospective Example 20 describes the use of the water-soluble ionic chromophores in two-photon fluorescence microscopy.

Examples 1-6

The following reaction scheme I is referred to in Examples 1-6.

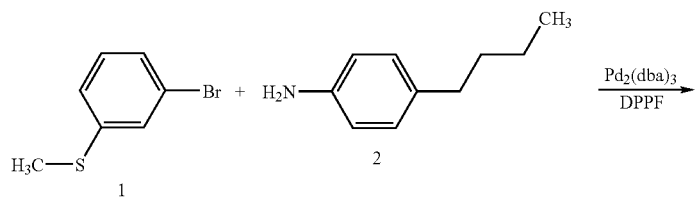

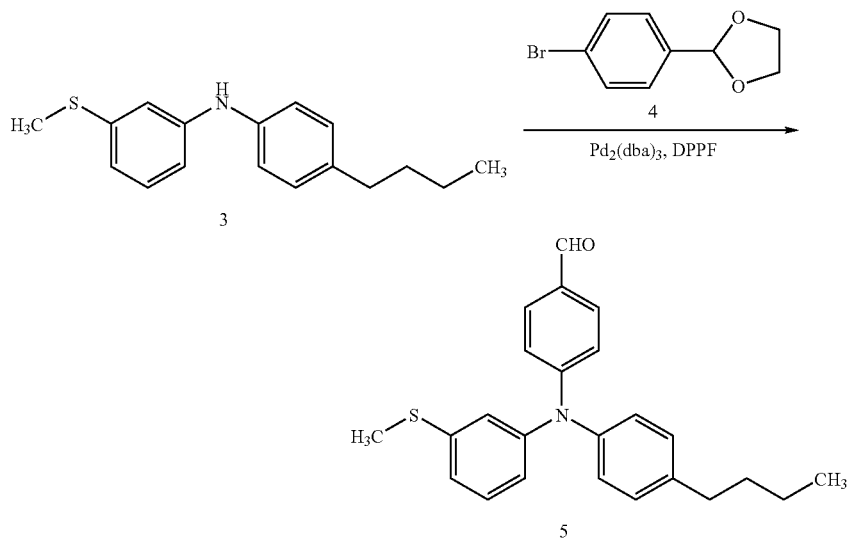

-continued
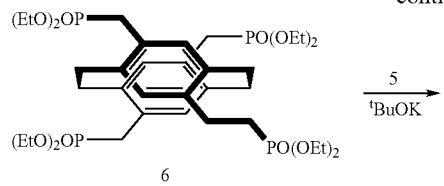
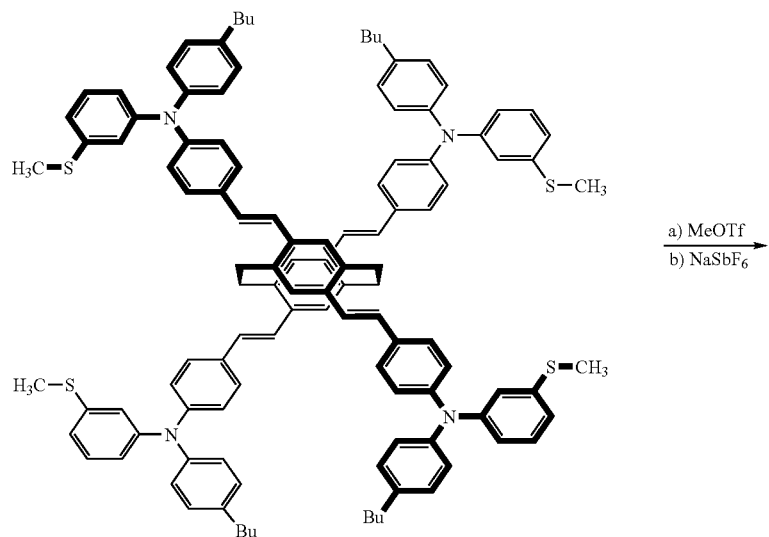
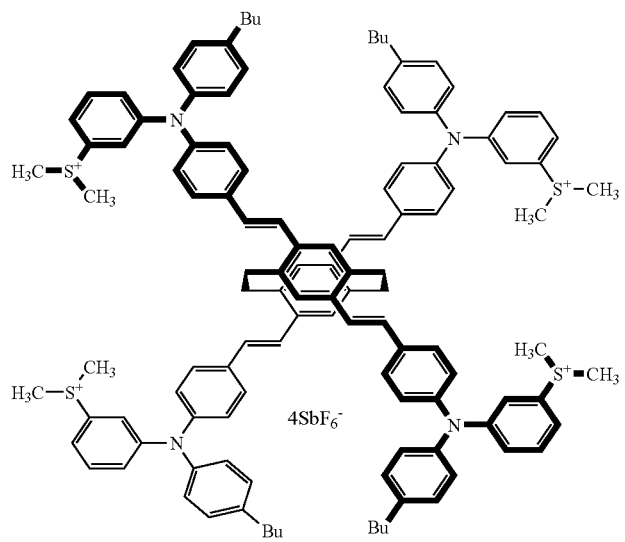

In Examples 1-6, the bold number in parenthesis following a compound name refers to the numbered compound in reaction scheme I.

Example 1

N-4-butylphenyl-N-3-methylthiophenylamine (3)

2.04 g (10.0 mmol) of 3-bromothioanisole (1), 1.65 g (11.0 mmol) of 4-butylaniline (2), 23 mg (0.025 mmol) of $Pd_2(dba)_3$, 42 mg (0.075 mmol) of 1,1'-bis(diphenylphosphino) ferrocene ("DPPF") and 1.34 g (14 mmol) of t-BuONa were dissolved in 20 mL of toluene. The mixture was stirred for 24 h at 90° C. After cooling to room temperature, it was diluted with 150 mL of diethyl ether and filtered. The solvent was evaporated and the residue was purified by liquid chromatography on silica gel (chloroform/hexane=1:1) to give 2.05 g of N-4-butylphenyl-N-3-methylthiophenylamine (3) (75%). $^1$H-NMR (400 MHz, $CDCl_3$): δ 7.19 (t, 8 Hz, 1H), 7.15 (m, 2 H), 7.06 (m, 2H), 6.96 (t, J=2 Hz, 1 H), 6.83 (m, 1 H), 6.813 (m, 1H), 2.63 (t, J=7.6 Hz, 2H), 2.49 (s, 3 H), 1.65(m, 2 H), 1.43 (tq, $J_1,J_2$=7.2 Hz, 2H), 1.00 (t, J=7.2 Hz, 3H). GC-MS: m/z=273 ($M^+$).

Example 2

4-(N-4-butylphenyl-N-3-methylthiophenyl-amino)-benzaldehyde (5)

A mixture of 1.65 g (6 mmol) of N-4-butylphenyl-N-3-methylthiophenylamine (3), 2.04 g (5.3 mmol) of 2-(4-bromophenyl)-[1,3]dioxolane (4), 23 mg (0.025 mmol) of $Pd_2(dba)_3$, 42 mg (0.075 mmol) of DPPF and 1.34 g (14 mmol) of t-BuONa in 20 mL of toluene was stirred for 24 h at 90° C. The reaction mixture was allowed to cool down to room temperature and was diluted with 150 mL diethyl ether. After filtration, the solvent was evaporated and the residue was purified by liquid chromatography on silica gel. The product was then dissolved in 20 mL of THF and 10 mL of 10% HCl was added. After stirring for 12 h at room temperature, the mixture was diluted with 150 mL of chloroform, washed twice with equal amounts of sat. $NaHCO_3$ aqueous solution and once with water. The organic phase was dried over $MgSO_4$, evaporated and the crude product was filtered over a short column of silica gel with chloroform. $^1$H-NMR (400 MHz, $CDCl_3$): δ 7.67 (m, 2 H), 7.245 (m, 1 H), 7.16 (m, 2H), 7.07(m, 2), 7.05 (m, 1 H), 7.03-6.99 (m, 3 H), 2.617 (t, J=7.6 Hz, 2H), 2.42 (s, 3 H), 1.62 (m, 2 H), 1.39 (tq,$J_1,J_2$=7.2Hz, 2H), 0.95 (t, J=7.2 Hz, 3H). GC-MS: m/z=375 ($M^+$).

Example 3

Para-cyclophane chromophore (7)

202 mg (0.25 mmol) of 4,7,12,15-tetra-(diethylphosphonatemethyl)paracyclophane (6) and 420 mg (1.125 mmol) of aldehyde (5) were dissolved in 4 mL of dry THF. 125 mg (1.125 mmol) of t-BuOK in 1 mL dry THF was added in one portion at 0° C. The mixture was allowed to warm up to room temperature and stirred for two days in the dark. Afterwards, the reaction mixture was diluted with 200 mL of methylene chloride and washed three times with equal amounts of brine. The organic phase was dried over $MgSO_4$ and the solvent was evaporated. The crude product was purified via liquid chromatography on silica gel (chloroform/hexane=2:3). The yield of chromophore (7) was 280 mg (68%). $^1$H-NMR (400 MHz, $CDCl_3$): δ 7.37-6.86 (m, 60 H), 3.55 (m, 4H), 2.88 (m, 4H), 2.59 (t, J=7.6 Hz, 8 H), 2.40 (s, 12 H), 1.61 (m, 8 H), 1.38 (m, 8H), 0.96 (t, J=7.6 Hz, 12H). MS (FAB): m/z=1694 ($M^+$), 845 (fragment-peak), 360 (fragment peak).

Example 4

Two-Photon Absorbing Chromophore (8)

41 mg (0.024 mmol) of chromophore (7) was dissolved in 1 mL dry methylene chloride. After cooling down to −78° C., 18 mg (0.11 mmol) of methyltriflate in 0.5 mL dry methylene chloride was added. The solution was allowed to warm up to room temperature and was stirred overnight. 5 mL of ether was added. The precipitate was filtered off and washed several times with ether. The solid was then dissolved in 1 mL of acetone and 53 mg (0.2 mmol) of sodium hexafluoroantimonate in 2 mL of water was added. After stirring for two hours, the solid was filtered off and washed with water and ether. This procedure was repeated three times. Yield of chromophore (8) was 15 mg (23%). $^1$H-NMR (200 MHz, acetone-$d_6$, triflate species): δ 7.71-7.10 (m, 60 H), 3.70 (broad peak, 2 H), 3.438 (24 H), 2.97 (broad peak, 2H), 2.63 (8 H), 1.16 (8 H), 1.39 (8H), 0.93 (12 H).

Example 5

Two-Photon Absorption (TPA) Cross Section Measurement

The two-photon absorption ("TPA") cross section of chromophore (8) was measured by non-linear transmission of femtosecond pulses through the sample solutions. A 100 fs duration ultra-short pulses of 1 kHz repetition rate regenerative Ti:Sapphire laser system (Integra, Quantronix) at the wavelength of 800 nm was used. To measure the transmission through the sample solution, the output energy ($I_{out}$) and input energy ($I_{in}$) were recorded by Si PIN photodiodes and processed by a gated integrator.

In this example, $I_{in}$ was varied from 0.3 $GW/cm^2$ to 39 $GW/cm^2$.

From the transmission curves, the TPA cross section were calculated according to the data processing methods well known in the art.

TPA cross sections measured in various solvents are provided in Table 1 for chromophore (8) and 4,4'-bis(diphenylamino)stilbene ("DPAS") (used as a reference material), along with chromophore (8) and DPAS solution concentrations.

TABLE 1

| Compounds | TPA cross section [GM] | Solvent | Concentration [mol/l] |
|---|---|---|---|
| pCp*[1] | 343 | acetone | $1.2E^{-4}$ |
| pCp*[1] | 363 | dimethyl sulfoxide | $2.2E^{-4}$ |
| DPAS*[2] | 9 | toluene | $4.0E^{-3}$ |

*[1]pCp: chromophore (8)
*[2]DPAS: 4,4'-bis(diphenylamino)stilbene

Example 6

The following epoxy monomer is used in this prospective example:

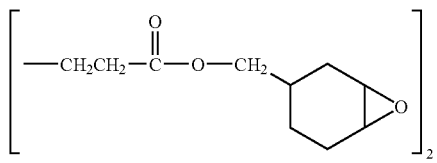

A solution of the epoxy monomer and chromophore (8) can be prepared in acetonitrile at a weight ratio of monomer to chromophore of about 100:1, for example. The mixture can be spin-coated onto glass slides at 1000 rpm for 10 sec. The spin-coated material can be illuminated under various conditions, such as by a Ti:Sapphire laser at a wavelength of 800 nm with a pulse width of about 100 fs, an input power of about 65 mW, and a repetition rate of about 1 kHz. The beam diameter can be about 1 mm, and the exposure time can be about 60 sec. The spin-coated material can be polymerized at the illuminated area.

Examples 7-12

In these prospective examples, the procedures of Examples 1-4 can be followed, *mutatis mutandis*, but with reagents that yield the chromophore of Formula VI with the moieties shown in Table II. Values for p and q depend on the particular moieties and the anion Y.

TABLE II

| Prospective Example | $D^1$ | | $D2$ | | $D3$ | |
|---|---|---|---|---|---|---|
| | $R^1$ | $R^2$ | $R^1$ | $R^2$ | $R^1$ | $R^2$ |
| 7 | H | Dimethyl-thiophenyl | H | Dimethyl-thiophenyl | H | Dimethyl-thiophenyl |
| 8 | $CH_3-(CH_2)n$, n = 1-5 | Dimethyl-thiophenyl | $CH_3-(CH_2)n$, n = 1-5 | Dimethyl-thiophenyl | $CH_3-(CH_2)n$, n = 1-5 | Dimethyl-thiophenyl |
| 9 | H | Dimethyl-iodophenyl | H | Dimethyl-iodophenyl | H | Dimethyl-iodophenyl |
| 10 | Nitrophenyl | Dimethyl-thiophenyl | Nitrophenyl | Dimethyl-thiophenyl | Nitrophenyl | Dimethyl-thiophenyl |
| 11 | Isobutyl | Dimethyl-iodophenyl | Isobutyl | Dimethyl-iodophenyl | Isobutyl | Dimethyl-iodophenyl |
| 12 | Butylphenyl | Hydroxymethyl-thiophenyl | Butylphenyl | Hydroxymethyl-thiophenyl | Butylphenyl | Hydroxymethyl-thiophenyl |

| Prospective Example | $D4$ | | $Z^1$ | $Z^2$ | $Z^3$ | $Z^4$ |
|---|---|---|---|---|---|---|
| | $R^1$ | $R^2$ | | | | |
| 7 | H | Dimethyl-thiophenyl | n = 1 | n = 1 | n = 1 | n = 1 |
| 8 | $CH_3-(CH_2)n$, n = 1 - 5 | Dimethyl-thiophenyl | n = 2 | n = 2 | n = 2 | n = 2 |
| 9 | H | Dimethyl-iodophenyl | n = 1 | n = 1 | n = 1 | n = 1 |
| 10 | Nitrophenyl | Dimethyl-thiophenyl | n = 3 | n = 3 | n = 3 | n = 3 |
| 11 | Isobutyl | Dimethyl-iodophenyl | n = 2 | n = 2 | n = 2 | n = 2 |
| 12 | Butylphenyl | Hydroxymethyl-thiophenyl | n = 1 | n = 1 | n = 1 | n = 1 |

Examples 13-20

Neutral compounds and ionic, water-soluble compounds referred to in Examples 13-20 are represented by the following formula and R groups:

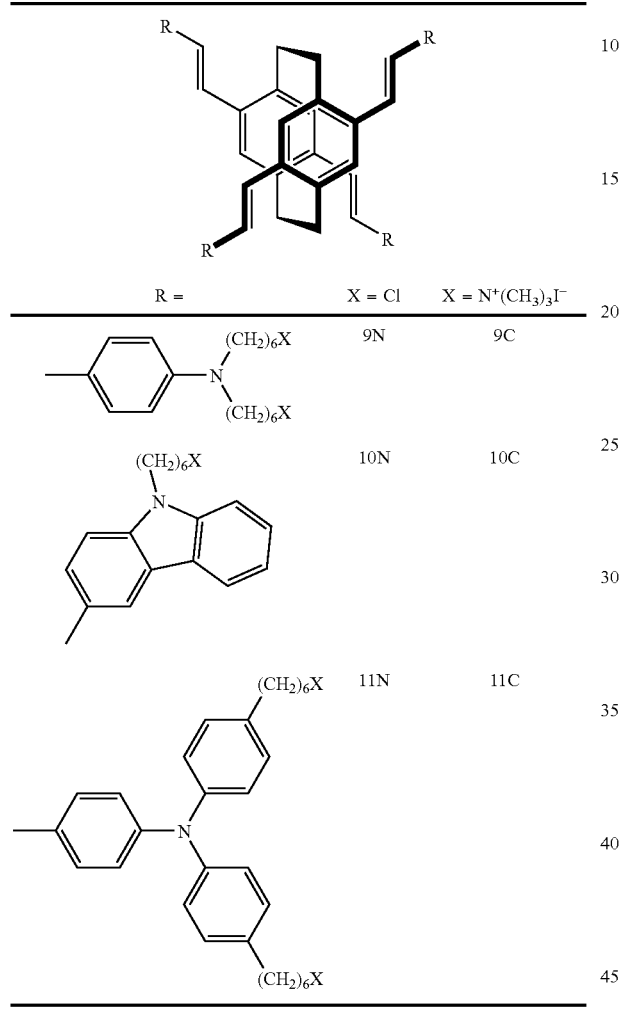

where the terminal R groups determine the donor ability of the nitrogen atom, and whether the molecule is neutral (N series) and soluble in non-polar organic solvents, or cationic (C series) and soluble in water.

The following reaction scheme II is referred to in Examples 13-20.

Scheme II

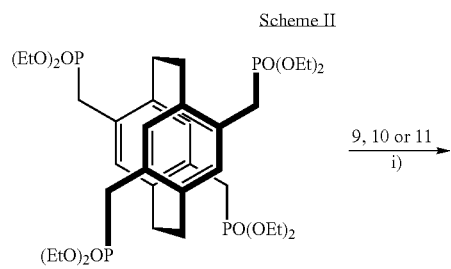

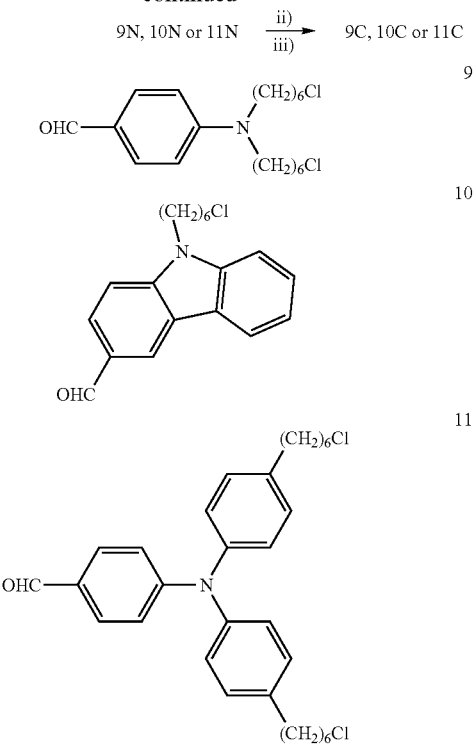

i) t-BuOK, THF, 0° C., 6 h; ii) NaI, acetone/MC, reflux, 2 days; iii) N(CH$_3$)$_3$, THF/H$_2$O, RT, 24 h.

In Examples 13-20, the bold number in parenthesis following a compound name refers to the numbered compound in reaction scheme II.

For synthesis, aniline was freshly purified by vacuum distillation. All other commercial chemicals were purchased from Aldrich and used as received. $^1$H and $^{13}$C-NMR spectra were collected on a Varian Unity 400 MHz (or 200 MHz) spectrometer. The UV-vis absorption spectra were recorded on a Shimadzu UV-2401 PC diode array spectrometer.

Photoluminescence spectra were obtained on a PTI Quantum Master fluorometer equipped with a Xenon lamp excitation source. The structures of the compounds including all intermediates were confirmed by common spectroscopic techniques such as $^1$H-NMR, $^{13}$C-NMR and mass spectroscopy and were in good agreement with the proposed structures.

Example 13

N,N-Bis(6'-chlorohexyl)-4-amino-benzaldehyde (9)

The synthetic route to amino-benzaldehyde (9) is presented in scheme III.

Scheme III

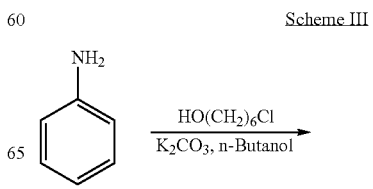

-continued

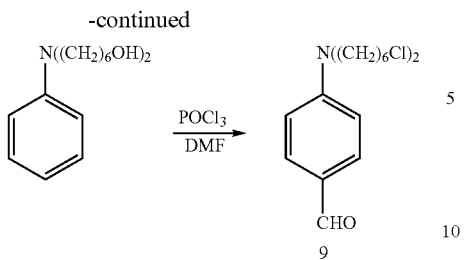

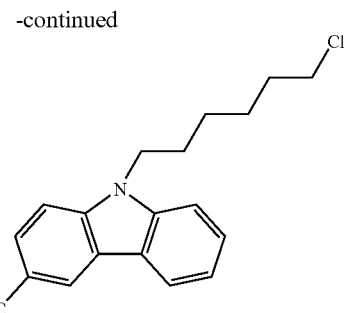

Using a modified literature method (Moon, K.-J.; Shim, H.-K.; Lee, K.-S.; Zieba, J.; Prasad, P. N. *Macromolcules* 1996, 29, 861), the reaction of aniline with 6-chloro-1-hexanol in butanol provided N,N-bis(6-hydroxyhexyl)-aniline in 70% yield. A 100 mL two-necked flask containing 15 mL of dry DMF was cooled down to 0° C. with an ice bath. To this solution, 4.7 g (30.7 mmol) of phosphorous oxychloride was added dropwise and the mixture was stirred for 30 min at 0° C. 3 g (10.2 mmol) of N,N-bis(6-hydroxyhexyl)-aniline in dry DMF (15 mL) was added to the above solution and heated to 90° C. for 2 hrs. The reaction solution was cooled down to room temperature, poured into ice water and neutralized to pH 6-8 with saturated sodium hydroxide aqueous solution. The resulting solution was extracted with methylene chloride and then dried over magnesium sulfate. The crude compound was purified by silica gel column chromatography (ethyl acetate/hexane=1:5) to yield 2.3 g (63%) of pure light brown oil, (9). $^1$H-NMR (200 MHz, CDCl$_3$): δ 9.71 (s, 1H, —CHO), 7.71 (d, 2H, J=9.0 Hz), 664 (d 2H, J=9.0 Hz), 3.55 (t, 4H, —CH$_2$Cl, J=6.6 Hz), 3.35 (t, 4H, —NCH$_2$—, J=7.6 Hz), 1.80 (m, 4H), 1.68-1.37 (m, 12H). $^{13}$C-NMR (100 MHz, CDCl$_3$): δ 190.2, 152.7, 132.5, 124.9, 110.9, 51.1, 45.2, 32.7, 27.2, 26.9, 26.5. HRMS (EI): m/z=357.1617 (M$^+$), Δ=2.6 ppm.

Example 14

N-(6'-chlorohexyl)carbazole-3-carboxaldehyde (10)

The synthetic route to carboxaldehyde (10) is presented in scheme IV.

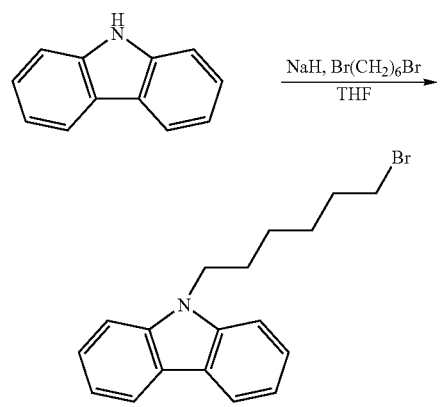

Scheme IV

To a two-necked flask containing carbazole (4.0 g, 23.9 mmol), 1,6-dibromohexane (29.2 g, 120 mmol) in 100 mL of anhydrous THF was added 0.86 g (35.8 mmol) of sodium hydride. This mixture was refluxed under nitrogen for 2 days. The reaction mixture was cooled down to room temperature and extracted with ethyl acetate. The non-reacted 1,6-dibromohexane and carbazole were removed by vacuum distillation (100° C./16 mmHg) and column chromatography (ethyl acetate/hexane=1:30), respectively. Pure N-(6-bromohexyl)carbazole was obtained in a white crystal (4 g, 51%). The 100 mL flask containing 30 mL of dry DMF was cooled down to 0° C. Phosphorous oxychloride (4.4 g, 28.7 mmol) was added dropwise maintaining the temperature below 5° C. The reaction mixture was stirred for 30 min. 1.9 g (5.75 mmol) of N-(6-bromohexyl)carbazole in 20 mL of dry DMF was added to the above solution and the temperature was slowly increased to 90° C. After the solution was heated for 2 days, it was cooled down to room temperature and poured into cold water. The pH of the solution was adjusted to around 7 with aqueous NaOH solution. The product was extracted with methylene chloride, dried over magnesium sulfate, and purified by silica gel column chromatography (ethyl acetate/hexane=1:5). A light brown crystal was obtained. (1.3 g, 72%). $^1$H-NMR (200 MHz, CDCl$_3$): δ 10.1 (s, 1H, —CHO), 8.62 (m, 1H), 8.17 (m, 1H), 8.02 (m, 1H), 7.59-7.27 (m, 4H), 4.36 (t, 2H, =NCH$_2$—, J=7.1 Hz), 3.50 (t, 2H, —CH$_2$Cl, J=6.4 Hz), 1.93 (m, 2H), 1.74 (m, 2H), 1.45 (m, 4H). $^{13}$C-NMR (100 MHz, CDCl$_3$): δ 191.9, 144.2, 141.3, 128.7, 127.3, 126.9, 124.2, 123.2, 123.1, 120.9, 120.5, 109.5, 109.0, 45.0, 43.4, 32.5, 29.0, 26.7, 26.6. HRMS (EI): m/z=313.1227 (M$^+$), Δ=2.1 ppm.

Example 15

N,N-Bis[4'-(6''-chlorohexyl)phenyl]-4-amino-benzaldehyde (11)

The synthetic route to amino-benzaldhyde (11) is presented in scheme V.

Scheme V

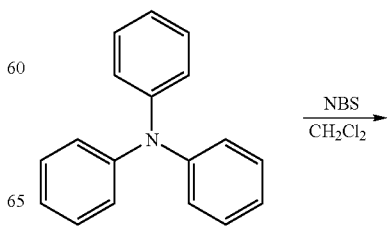

-continued

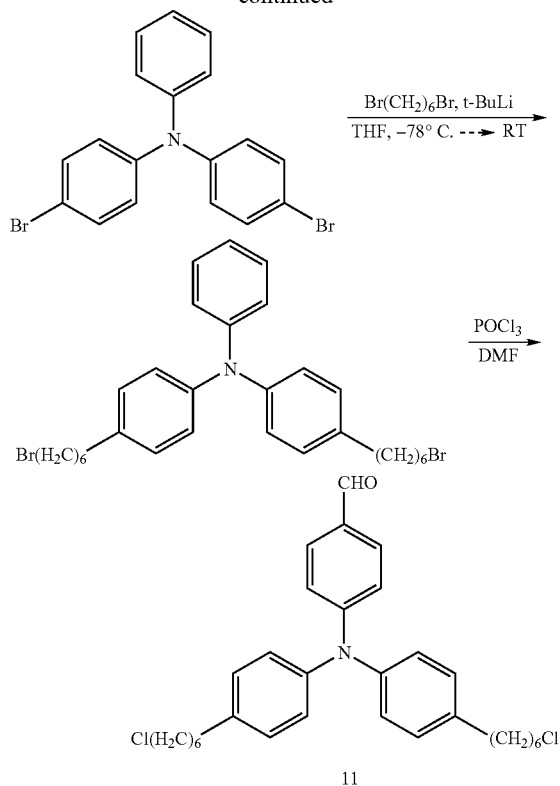

4,4'-dibromotriphenylamine was synthesized according to the method reported in Lee, H. J.; Sohn, J.; Hwang, J.; Park, S. Y.; Choi, H.; Cha, M. *Chem. Mater.* 2004, 16, 456. The solution containing 4,4'-dibromotriphenylamine (1.9 g, 4.7 mmol) and an excess of dry 1,6-dibromohexane (11.5 g, 47 mmol) in 50 mL of dry THF was cooled down to −78° C. 8.3 mL (3 eq.) of t-butyl lithium (in pentane, 1.7 M) was added dropwise and the reaction mixture was gradually allowed to reach room temperature for 4 hrs. The resulting solution was quenched with water, evaporated under reduced pressure, and extracted with methylene chloride. The organic phase was dried over magnesium sulfate and concentrated. Non-reacted 1,6-dibromohexane was removed by vacuum distillation and the pure bis[4-(6'-bromohexyl)phenyl]phenylamine was obtained by column chromatography (methylene chloride/hexane=1:10) in a colorless oil (1.7 g, 63%). The 100 mL flask containing 20 mL of dry DMF was cooled down to 0° C. Phosphorous oxychloride (0.75 g, 4.9 mmol) was added dropwise maintaining the temperature below 5° C. The reaction mixture was stirred for 30 min. 0.93 g (1.62 mmol) of bis[4-(6'-bromohexyl)phenyl]phenylamine in 10 mL of dry DMF was added to the above solution and the temperature was slowly increased to 90° C. After the solution was heated overnight, it was cooled down to room temperature and poured into cold water. The pH of the solution was adjusted to around 7 with aqueous NaOH solution. The product was extracted with methylene chloride, dried over magnesium sulfate, and purified by silica gel column chromatography (ethyl acetate/hexane=1:10). The product yield was 0.65 g (78%). $^1$H-NMR (200 MHz, CDCl$_3$): δ 9.78 (s, 1H, —CHO), 7.65 (d, 2H, J=8.8 Hz), 7.15 (d, 4H, J=8.6 Hz), 7.08 (d, 4H, J=8.8 Hz), 6.95 (d, 2H, J=8.8 Hz), 3.55 (t, 4H, —CH$_2$Cl, J=6.7 Hz), 2.61 (t, 4H, ArCH$_2$—, J=7.7 Hz), 1.80 (m, 4H), 1.65 (m, 4H), 1.44 (m, 8H). $^{13}$C-NMR (100 MHz, CDCl$_3$): δ 190.5, 131.5, 129.8, 126.5, 126.2, 118.4, 45.3, 35.5, 32.7, 31.4, 28.7, 26.9. HRMS (EI): m/z=509.2253 (M$^+$), Δ=0.1 ppm.

Example 16

General Procedure for 9N-11N

A 50 mL two-necked flask charged with 4,7,12,15-tetra-(diethylphosphonatemethyl) paracyclophane (0.5 mmol) and 5 eq. of aldehyde compound (9, 10 or 11, 2.5 mmol) in 20 Ml of dry THF was cooled down to 0° C. with an ice bath. To the above solution, 2.5 mL (5 eq.) of potassium tert-butoxide (in THF, 1M) was added dropwise at 0° C. The reaction mixture was stirred for 6 hrs at 0° C. and then quenched with water. The solvent was removed under reduced pressure and the resulting mixture was diluted with methylene chloride, washed with water and brine, and dried over magnesium sulfate. The crude compound was purified by silica gel column chromatography.

4,7,12,15-Tetra[N,N-bis(6''-chlorohexyl)-4'-aminostyryl]-[2,2]paracyclophane (9N)

The crude product was purified by silica gel column chromatography (chloroform/hexane=1:1) to give pure 9N in 60% yield. $^1$H-NMR (400 MHz, CDCl$_3$): δ 7.41 (d, 8H, J=8.6 Hz), 6.99 (d, 4H, —CH═CH—, J=15.6 Hz), 6.96 (s, 4H), 6.86 (d, 4H, —CH═CH—, J=15.6 Hz), 6.67 (d, 8H, J=8.6 Hz), 3.57 (t, 16H, —CH$_2$Cl, J=6.6 Hz), 3.51 (m, 4H, bridge proton of pCp), 3.34 (br m, 16H, —NCH$_2$—), 2.84 (m, 4H, bridge proton of pCp), 1.83 (m, 16H), 1.67 (m, 16H), 1.53 (m, 16H), 1.41 (m, 16H). $^{13}$C-NMR (100 MHz, CDCl$_3$): δ 147.7, 137.3, 136.8, 128.2, 127.6, 125.8, 121.6, 112.0, 51.2, 45.3, 33.4, 32.8, 27.5, 27.0, 26.7. MS (FAB): m/z=1626 (M$^+$).

4,7,12,15-Tetra[(N-(6''-chlorohexyl)carbazol-3'-yl)vinyl]-[2,2]paracyclophane (10N)

The compound was purified by column chromatography (methylene chloride/hexane=1:2) in 60% yield. $^1$H-NMR (200 MHz, CDCl$_3$): δ 8.14 (s, 4H), 7.86 (m, 8H), 7.53-7.30 (m, 20H), 7.23 (s, 4H), 7.05 (m, 4H), 4.37 (t, 8H, ═NCH$_2$—, J=6.9 Hz), 3.75 (m, 4H, bridge proton of pCp), 3.50 (t, 8H, —CH$_2$Cl, J=6.5 Hz), 3.08 (m, 4H, bridge proton of pCp), 1.96 (m, 8H), 1.75 (m, 8H), 1.47 (m, 16H). $^{13}$C-NMR (100 MHz, CDCl$_3$): δ 141.0, 140.3, 137.7, 137.1, 129.8, 129.5, 128.0, 126.0, 124.3, 123.4, 123.1, 120.9, 119.8, 119.6, 119.2, 109.3, 108.9, 45.2, 43.2, 33.4, 32.6, 29.1, 26.8. MS (FAB): m/z=1447 (M$^+$).

4,7,12,15-Tetra[N,N-bis(4''-(6'''-chlorohexyl)phenyl)-4'-aminostyryl]-[2,2]paracyclophane (11N)

The compound was purified by column chromatography (methylene chloride/hexane=1:3) in 61% yield. $^1$H-NMR (200 MHz, CDCl$_3$): δ 7.36 (d, 8H, J=8.6 Hz), 7.2-7.0 (m, 48H), 6.90 (d, 4H, —CH═CH—, J=16 Hz), 3.56 (t and br, 20H, —CH$_2$Cl (J=6.7 Hz) and bridge proton of pCp), 2.88 (br, 4H, bridge proton of pCp), 2.60 (t, 16H, ArCH$_2$—, J=7.6 Hz), 1.82 (m, 16H), 1.66 (m, 16H), 1.46 (m, 32H). $^{13}$C-NMR (100 MHz, CDCl$_3$): δ 147.7, 145.5, 137.7, 137.5, 136.8, 131.6, 129.3, 128.1, 127.5, 124.6, 123.8, 123.2, 45.3, 35.4, 33.4, 32.7, 31.5, 28.8, 26.9. MS (FAB): m/z=2234 (M$^+$).

Example 17

General Procedure for 9C-11C

A round-bottomed flask was charged with 0.1 mmol of 9N, 10N or 11N in 5 mL of dry methylene chloride and a large excess of sodium iodide (30 mmol) in 200 mL of dry acetone. The reaction solution was heated to reflux for 2 days. After the reaction was completed, the solvent was removed under reduce pressure and the residue was diluted with methylene chloride, washed with brine, and dried over anhydrous magnesium sulfate. The crude compound was purified by column chromatography in 70-80% yield. After Chloride/iodide exchange, to a solution of each compound with iodide functionality (0.05 mmol) in 20 mL of THF, was added an excess of condensed trimethylamine (2 mL) using a dry ice/acetone filled gas condenser at −78° C. The reaction mixture was allowed to slowly warm up to room temperature and stirred for 12 hrs. A small amount of water was added to the above solution to dissolve the precipitated compounds and the reaction solution was cooled down to −78° C. An excess of condensed trimethylamine (2 mL) was added again and the resulting solution was allowed to reach room temperature and stirred for additional 12 hrs. After the reaction was completed, the excess of trimethylamine and solvent were removed under reduced pressure. The remaining water solution was washed with diethyl ether and chloroform, and finally water was removed by vacuum distillation. A crude product was dissolved in a minimum amount of hot methanol and precipitated into diethyl ether several times.

The 4,7,12,15-Tetra[N,N-bis(6"-(N,N,N-trimethylammonium)hexyl)-4'-aminostyryl]-[2,2]paracyclophane octaiodide (9C) product had the following characteristics. Yield: 85%.

$^{1}$H-NMR (400 MHz, DMSO-$d_6$): δ 7.37 (d, 8H, J=8.8 Hz), 6.98 (d, 4H, —CH═CH—, J=16.0 Hz), 6.80 (s, 4H), 6.69 (m, 12H), 3.53 (br m, 4H, bridge proton of pCp), 3.35 (m, 32H), 3.07 (s, 72H, —N$^+$(CH$_3$)$_3$I$^-$), 2.73 (br m, 4H, bridge proton of pCp), 1.70 (br m, 16H), 1.59 (br m, 16H), 1.37 (br m, 32H). $^{13}$C-NMR (100 MHz, DMSO-$d_6$): δ 147.3, 136.9, 136.3, 127.9, 127.0, 124.6, 120.9, 111.7, 65.2, 52.2, 50.1, 32.7, 26.8, 26.1, 25.8, 22.2. MS (ESI/TOF): 1287.6 (M$^{2+}$-2I), 816.1 (M$^{3+}$-3I), 580.3 (M$^{4+}$-4I).

The 4,7,12,15-Tetra[(N-(6"-(N,N,N-trimethylammonium)hexyl)carbazol-3'-yl)vinyl][2,2]paracyclophane octaiodide (10C) product had the following characteristics. Yield: 90%.

$^{1}$H-NMR (200 MHz, DMSO-$d_6$): δ 8.13 (s, 4H), 7.93 (d, 4H, J=8.8 Hz), 7.70 (m, 12H), 7.43 (m, 8H), 7.14 (d, 4H, —CH═CH—, J=16 Hz), 7.09 (s, 4H), 6.93 (m, 4H), 4.49 (br, 8H, ═NCH$_2$—), 3.73 (br, 4H, bridge proton of pCp), 3.21 (m, 8H, —CH$_2$N$^+$(CH$_3$)$_3$I$^-$), 2.99 (s,40H, —N$^+$(CH$_3$)$_3$I$^-$ and bridge proton of pCp), 1.86 (br, 8H), 1.58 (br, 8H), 1.33 (br, 16H). $^{13}$C-NMR (100 MHz, DMSO-$d_6$): δ 140.4, 139.7, 137.5, 136.9, 129.6, 128.9, 127.7, 125.9, 124.2, 123.5, 122.5, 122.1, 120.3, 119.5, 118.8, 109.8, 109.5, 65.3, 52.1, 42.3, 32.6, 28.5, 26.1, 25.7, 22.1. MS (ESI/TOF): m/z=897 (M$^{2+}$-2I), 556 (M$^{3+}$-3I), 385 (M$^{4+}$-4I).

The 4,7,12,15-Tetra[N,N-bis(4"-(6'''-(N,N,N-trimethylammonium)hexyl)phenyl)-4'aminostyryl]-[2,2]paracyclophane octaiodide (11C) product had the following characteristics.

Yield: 90%. $^{1}$H-NMR (200 MHz, DMSO-$d_6$): δ 7.39 (d, 8H, J=8.4 Hz), 7.17 (d, 4H, —CH═CH—, J=13.8 Hz), 7.12 (d, 16H, J=8.6 Hz), 6.94 (d, 16H, J=8.4 Hz), 6.9-6.82 (m, 12H), 6.76 (d, 4H, —CH═CH—, J=13.8 Hz), 3.55 (br, 4H, bridge proton of pCp), 3.27 (m, 16H, —CH$_2$N$^+$(CH$_3$)$_3$I$^-$), 3.05 (s, 72H, —N$^+$(CH$_3$)$_3$I$^-$), 2.84 (br, 4H, bridge proton of pCp), 2.52 (br 16H), 1.63 (br, 32H), 1.34 (br, 32H). $^{13}$C-NMR (100 MHz, DMSO-$d_6$): δ 146.9, 144.8, 137.5, 137.2, 136.6, 131.2, 129.3, 128.1, 127.8, 124.1, 123.7, 122.4, 65.3, 52.2, 34.5, 32.4, 30.8, 28.4, 25.7, 22.1. MS (ESI): m/z=1019 (M$^{3+}$-3I), 732 (M$^{4+}$-4I), 560 (M$^{5+}$-5I), 446 (M$^{6+}$-6I).

Example 18

Two-photon absorption ("TPA") spectra of the neutral and ionic chromophores were measured using two-photon induced fluorescence ("TPIF") spectroscopy (Xu, C.; Webb, W. W. J. Opt. Soc. Am. B 1996, 13, 481). The samples were excited via a TPA process by directing a tightly collimated, high intensity laser beam on a sample. The emission from the sample was collected at a 90° angle by a high numerical aperture lens and directed to a spectrometer's entrance slit. The radiation dispersed by the spectrometer was detected by a thermoelectrically cooled charge coupled device ("CCD") camera (Roper Scientific Spec10:100B/TE). Excitation pulses with typical duration of 90 fs and energy of ~6 nJ within the spectral range 700-1000 nm were produced by a mode-locked Ti:Sapphire laser (Spectraphysics Tsunami) with a repetition rate of 82 MHz. For the spectral range 620-700 nm, a femtosecond optical parametric amplifier ("OPA") has been used. Signal output of the OPA (Spectraphysics OPA-800C) was upconverted into the visible range of spectrum using the second harmonic generation ("SHG") process in β-barium borate crystal, which yielded 120 fs pulses with energy of ~30 μJ and a repetition rate of 1 kHz. A neutral density filter wheel was used to attenuate the energy of the laser pulses down to the desirable level.

Two-photon induced fluorescence spectra of the standard and the samples were recorded at the same excitation wavelength. The ratio of the integrated fluorescence intensities for the reference and studied samples can be expressed as $$\frac{I}{I_{ref}} = \frac{\eta \delta c}{\eta_{ref} \delta_{ref} c_{ref}} \frac{P^2}{P_{ref}^2} K$$

where the index ref denotes values related to the reference measurements. The signal intensity collected by detector is denoted as I and η is the fluorescence quantum yield. The number density of the molecules in solution is denoted as c. $\delta_{ref}$ means the TPA cross section of the reference molecule. All experimental parameters were assumed to be identical during the whole series of measurements, except the power of the pump radiation (P) and sample specific parameters, η and c. K is a correction factor taking into account the difference in refractive indices of the solvents of the studied samples and the reference material. It depends on the excitation beam geometry. In our case of nearly-collimated beams, K=$n_{ref}^2/n^2$.

Molar concentrations of the compounds were determined from optical absorption spectra, using molar absorptivity values supplied by the compound manufacturer or obtained from volumetric measurements. In all measurements, the concentration of the material was adjusted around $10^{-5}$ M, in order to avoid self-quenching of emission. Fluorescence quantum yields were measured relative to fluorescein and were verified using a reference-less technique (Greenham, N. C.; Samuel, I. D. W.; Hayes, G. R.; Phillips, R. T.;

Kessener, Y. A. R. R.; Moratti, S. C.; Homes, A. B.; Friend, R. H. *Chem. Phys. Lett.* 1995, 241, 89). Both absorption and emission spectra of samples were monitored during the whole series of measurements. Degassed samples did not exhibit any sign of degradation within the scope of the experiment.

As reference materials in the spectral range of 700-900 nm, three laser dyes were used: Coumarin 503 (aka Coumarin 307, purchased from Exciton Inc.); Fluorescein (purchased from Acros Inc.); and Rhodamine 610 (aka Rhodamine B, purchased from Exciton Inc.). Coumarin 503 and Rhodamine 610 were dissolved in methanol, and fluorescein was prepared in water (pH=11). p-bis(o-methylstyryl)benzene in cyclohexane ($10^{-4}$ M) was used as a reference for measurements in the spectral range below 700 nm.

TPIF studies were performed in low excitation power regime, which was verified by measuring fluorescence intensity pump dependence. In all cases, it was very close to pure quadratic function. This indicates that fluorescence had not been excited via regular single-photon absorption and that a pure non-linear process was measured.

Figure 2:
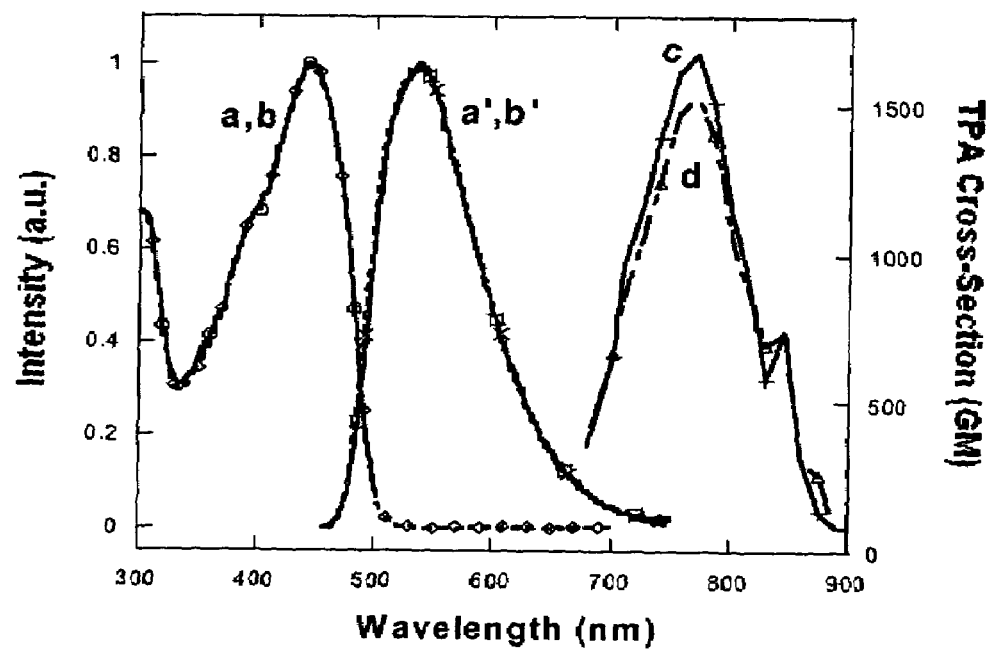
FIG. 2 is a graph showing normalized absorption and emission spectra, and two-photon absorption spectra, of various chromophores.

The TPA behaviors in toluene for 9N, 10N and 11N and in water for 9C, 10C and 11C were investigated. In all cases, the chromophores demonstrated a substantial decrease of TPA cross section in water without any significant change of TPA maximum and band shape. This is shown in FIG. 1, where the two-photon absorption spectra of 9N (a), 10N (b) and 11N (c) in toluene, and 9C (a'), 10C (b') and 11C (c') in water are provided. The absorption and emission spectra of N and C series were confirmed in the same solvent, DMSO as shown in FIG. 2, where the normalized absorbance and emission spectra of 11N (a and a', respectively) and 11C (b and b', respectively) are shown along with the two-photon absorption spectra of 11N (c) and 11C (d) in DMSO. The DMSO solvent is of intermediate polarity between water and toluene, and can dissolve both the neutral and cationic molecules. The neutral and cationic counterparts of the paracyclophane based chromophores showed almost identical absorption/PL and TPA spectra in DMSO, demonstrating that the terminal end group has little effect on the optical properties of the compounds.

A summary of the absorption, photoluminescence and TPA results in toluene and water is provided in Table III.

TABLE III

|      | Solvent | $\lambda_{abs}$ | $\lambda_{em}$ | $\eta^a$ | $\lambda_{TPA}$ | $\delta$ (GM)$^b$ |
|------|---------|------|------|------|------|------|
| 9N   | Toluene | 434  | 486  | 0.92 | 725  | 1290 |
| 9C   | Water   | 435  | 553  | 0.04 | 725  | 370  |
| 10N  | Toluene | 420  | 468  | 0.95 | 700  | 1690 |
| 10C  | Water   | 410  | 505  | 0.42 | 700  | 700  |
| 11N  | Toluene | 441  | 492  | 0.92 | 770  | 2080 |
| 11C  | Water   | 431  | 537  | 0.52 | 750  | 690  |

$^a$PL quantum yields were measured at $10^{-6}$ M relative to fluorescein.
$^b$Peak TPA cross section at $\lambda_{TPA}$.

Example 19

The following tri-acrylate monomer is used in this prospective example of radical photo-polymerization:

(H$_2$C=CHCO$_2$CH$_2$)$_3$CC$_2$H$_5$ (TMPTA)

The two-photon photo-polymerization formulation can comprise 1 wt % of chromophore 9N, 10N or 11N, 29 wt % of a polymer binder such as poly(styrene-co-acrylonitrile) (75:25), and 70 wt % of the reactive trifunctional acrylate monomer TMPTA in dioxane for example. The mixture can be spin-coated onto glass slides at 1000 rpm for 10 sec. The spin-coated material can be illuminated under various conditions, such as by a Ti:Sapphire laser at a wavelength of 750 nm with a pulse width of 100 fs, a pulse energy of 100 μJ, and a repetition rate of 1 kHz. The beam diameter can be about 1 μm, and the exposure time can be max. 60 sec, for example. The spin-coated material can be polymerized at the illuminated area.

Example 20

In this prospective example of two-photon fluorescence microscopy, living cells such as rat basophilic leukemia (RBL) cells can be incubated with a cell-compatible medium, such as a buffer or a liquid medium, containing water-soluble TPA fluorophore 10C or 11C at a concentration of about $10^{-6}$ M. A three dimensional fluorescence image can be obtained by using a modified Bio-Rad MRC-600 confocal microscope to scan an excitation beam of, for example, about 720 nm, ~120 fs pulse width, and 1-5 mW on the cells through a ×40/numerical aperture oil-immersion objective. Epifluorescence can be collected by using non-descanned external detection into fixed wavelength detection. A 3D two-photon fluorescence image can be obtained by scanning the depth (z) and lateral (x,y) dimensions of the sample with respect to the focus of the laser beam. The axial direction (z) scan can be accomplished by translating the sample using a stepping motor-controlled translation stage having a resolution of 0.1 μm/step. The lateral scan (x,y) can be performed with a second translation stage with same stepping resolution.

The following publications are hereby incorporated by reference:

1. Moon, K.-J.; Shim, H.-K.; Lee, K.-S.; Zieba, J.; Prasad, P. N. *Macromolcules* 1996, 29, 861.
2. Lee, H. J.; Sohn, J.; Hwang, J.; Park, S. Y.; Choi, H.; Cha, M. *Chem. Mater.* 2004, 16, 456.
3. Xu, C.; Webb, W. W. *J. Opt. Soc. Am. B* 1996, 13, 481.
4. Greenham, N. C.; Samuel, I. D. W.; Hayes, G. R.; Phillips, R. T.; Kessener, Y. A. R. R.; Moratti, S. C.; Homes, A. B.; Friend, R. H. *Chem. Phys. Lett.* 1995, 241, 89.

What is claimed is:

1. A compound of the formula

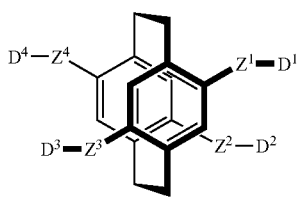

wherein
D$^1$, D$^2$, D$^3$ and D$^4$ are the same or different and are each independently selected from the group consisting of (a)

wherein
i) R¹ and R² are each independently hydrogen or a substituted alkyl or aryl group, or
ii) R¹ and R² taken together with the nitrogen atom to which they are attached form a substituted or non-substituted hetorocycle which is saturated or nonsaturated; and

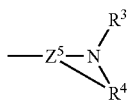
(b)

wherein Z⁵ is a substituted or non substituted stilbenoid group of the formula

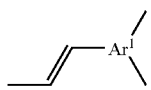

wherein Ar¹ is a substituted or non-substituted cyclic aromatic group providing two carbon atoms through which R⁴ and N are respectively attached to Z⁵, R³ is hydrogen or a substituted or non-substituted alkyl or aryl group, and R⁴ and N taken together with the carbon atoms of Z⁵ to which R⁴ and N are attached form a substituted or non-substituted heterocycle which is saturated or nonsaturated;
wherein Z¹, Z², Z³ and Z⁴ are each independently a substituted or non-substituted stilbenoid group of the formula

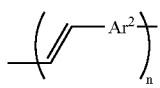

where Ar² is and arylene group, and n is an integer from 1 to 5 in (a) or from 0 to 4 in (b);
each of Z¹, Z², Z³,Z⁴, Z⁵, R¹, R², R³, and R⁴ can be independently substituted with one or more halogen, alkyl, aryl, alkoxy, aryloxy, cyano, nitro, aroyl, acyl or hydroxy groups.

2. The compound of claim 1 wherein
(a) at least one of D¹, D², D³ and D⁴ is substituted on R¹, R², R³ or R⁴ with a sulfonium, ammonium, selenium, iodonium or phosphonium group of respective formula —S⁺X¹X², —N⁺X¹X²X³, —Se⁺X¹X², —I⁺X¹X² and —P⁺X¹X²X³ wherein X¹, X² and X³ are each independently a substituted or non-substituted alkyl or aryl group, and wherein each of X¹, X² and X³ can be independently substituted with one or more halogen, alkyl, aryl, alkoxy, aryloxy, cyano, nitro, aroyl, acyl or hydroxy groups; and
(b) the compound of claim 1 further includes an anion selected from the group consisting of F⁻, Cl⁻, Br⁻, I⁻, CN⁻, SO4²⁻, PO4³⁻, CH₃CO₂⁻, CF₃SO₃, BF₄⁻, PF₆⁻, SbF₆⁻, AsF₆⁻, SbCl₄⁻, ClO₃⁻, ClO₄³¹, NO₂⁻, NO₃⁻ and B(aryl)₄⁻ in an amount sufficient to balance the chromophore's cationic charge.

3. The compound of claim 1 wherein D¹, D², D³ and D⁴ are the same or different and are each a group according to (a)(i), wherein R¹ and R² are substituted alkyl groups.

4. The compound of claim 1 wherein R¹, R² and R³ are each substituted with one or more halogen groups.

5. The compound of claim 1 wherein D¹, D², D³ and D⁴ are the same or different and are each a group according to (a)(i), wherein R¹ and R² are asyl groups.

6. The compound of claim 1 wherein D¹, D², D³ and D⁴ are the same or different and are each a group according to (b), where Ar¹ is a benzene group, R³ is an alkyl group, and R⁴ and N taken together with the carbon atoms of Z⁵ to which R⁴ and N are attached form an aromatic heterocycle.

7. A compound of the formula

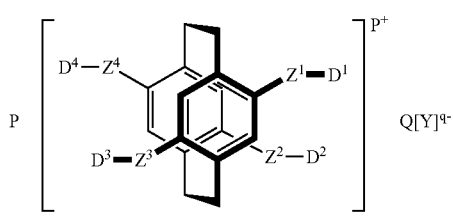

wherein
D¹, D², D³ and D⁴ are the same or different and are each independently selected from the group consisting of

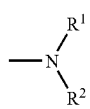
(a)

wherein
i) R¹ and R² are each independently hydrogen or a substituted alkyl or aryl group, or
ii) R¹ and R² taken together with the nitrogen atom to which they are attached form a substituted or non-substituted heterocycle which is saturated or nonsaturated; and

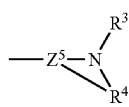
(b)

wherein Z⁵ is a substituted or non substituted stilbenoid group of the formula

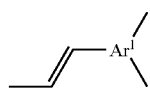

wherein Ar¹ is a substituted or non-substituted cyclic aromatic group providing two carbon atoms through which R⁴ and N are respectively attached to Z⁵, R³ is hydrogen or a substituted or non-substituted alkyl or aryl group, and R⁴ and N taken together with the carbon atoms of Z⁵ to which R⁴ and N are attached form a substituted or non-substituted heterocycle which is saturated or nonsaturated;

wherein at least one of $D^1$, $D^2$, $D^3$ and $D^4$ is substituted on $R^1$, $R^2$, $R^3$ or $R^4$ with a sulfonium, ammonium, selenium, iodonium or phosphonlium group of respective formula $-S^+X^1X^2$, $-N^+X^1$, $X^2X^3$, $-Se^+X^1$, $X^2$, $-I^+X^1X^2$ and $-P^+X^1X^2X^3$ wherein $X^1$, $X^2$ and $X^3$ are each independently a substituted or non-substituted alkyl or aryl group, and wherein each of $X^1$, $X^2$ and $X^3$ can be independently substituted with one or more halogen, alkyl, aryl, alkoxy, aryloxy, cyano, nitro, aroyl, acyl or hydroxy groups;

$Z^1$, $Z^2$, $Z^3$ and $Z^4$ are each independently a substituted or non-substituted stilbenoid group of the formula

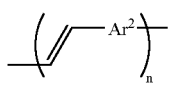

where $Ar^2$ is an arylene group, and n is an integer from 1 to 5 in (a) or from 0 to 4 in (b);

Y is an anion selected from the group consisting of $F^-$, $Cl^-$, $Br^-$, $I^-$, $CN^-$, $SO_4^{2-}$, $PO_4^{3-}$, $CH_3CO_2^-$, $CF_3SO_3^-$, $BF_4^-$, $PF_6^-$, $SbF_6^{31}$, $AsF_6^-$, $SbCl_4^-$, $ClO_3^-$, $ClO_4^-$, $NO_2^-$, $NO_3^-$ and $B(aryl)_4^-$;

p is an integer equal to the cationic charge of the chromophore portion of the compound;

q is an integer equal to the charge on the anion;

Q and P are integers that satisfy the relationship qQ=pP; and wherein each of t, $Z^1$, $Z^2$, $Z^3$, $Z^4$, $Z^5$, $R^1$, $R_2$, $R_3$, and $R^4$ can be independently substituted with one or more halogen, alkyl, aryl, alkoxy, aryloxy, cyano, nitro, aroyl, acyl or hydroxy groups.

8. The compound of claim 7 wherein each of $D^1$, $D^2$, $D^3$ and $D^4$ is substituted with at least one ammonium or phosphonium group, rendering the compound water-soluble.

9. The compound of claim 8 wherein each of $D^1$, $D^2$, $D^3$ and $D^4$ is substituted with two ammonium or phosphonium groups.

10. The compound of claim 7 wherein $D^1$, $D^2$, $D^3$ and $D^4$ are the same or different and are each a group according to (a)(i), wherein $R^1$ and $R^2$ are alkyl groups.

11. The compound of claim 7 wherein $D^1$, $D^2$, $D^3$ and $D^4$ are the same or different and are each a group according to (a)(i), wherein $R^1$ and $R^2$ are aryl groups.

12. The compound of claim 7 wherein $D^1$, $D^2$, $D^3$ and $D^4$ are the same or different and are each a group according to (b), where $Ar^1$ is a benzene group, $R^3$ is an alkyl group, $R^4$ and N taken together with the carbon atoms of $Z^5$ to which $R^4$ and N are attached form an aromatic heterocycle.

13. A compound of the formula

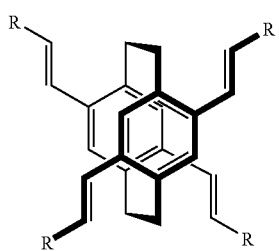

wherein R, is selected from the group consisting of

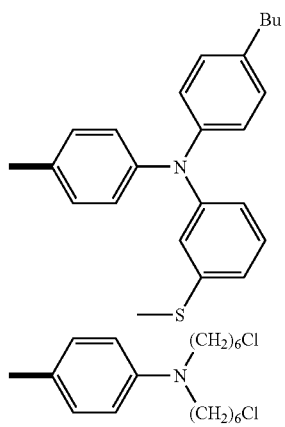

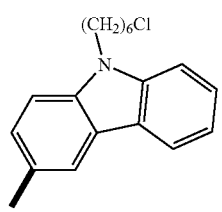

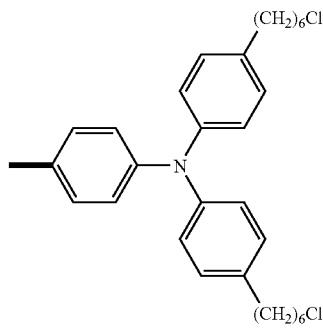

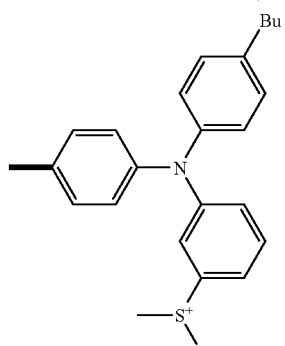

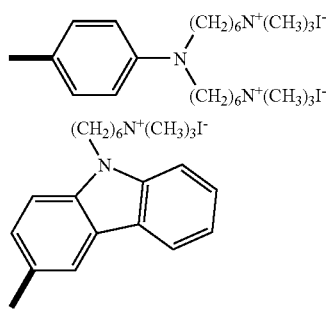

-continued

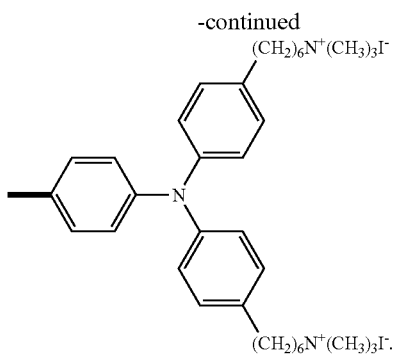

14. A composition for biological imaging, comprising a cell-compatible medium and a water-soluble compound of claims 8 or 13.

15. A method of biological imaging by two-photon fluorescence microscopy, comprising:
(a) incubating a water-soluble compound of claims 8 or 13 with a living cell;
(b) scanning the incubated cells with a confocal microscope to provide a three dimensional, two-photon induced fluorescence image.

16. A method of preparing compound according to claim 1, the method comprising reacting a paracyclophane tetraphosphonate with an amino benzaldehyde selected from the group consisting of
(i) a 4-(N,N-diphenyl-axnino) benzaldehyde,
(ii) a N,N-Bis(6'-chlorohexyl)-4-amino-benzaldehyde,
(iii) a carbazole-3-carboxaldehyde, and
(iv) a 4-9'-carbazolylbenzaldehyde,
thereby producing a paracyclophane chromophore having stilbenoid groups.

17. The method of claim 16 wherein the 4-(N,N-diphenylamino) benzaldehyde is a 4-(N-4-butylphenyl-N-3-methyltiophenyl-amino)-benzaldehyde or a N,N-Bis[4'-(6"-chlorohexyl)phenyl]-4-amino-benzaldhyde, and the carbazole-3-carboxaldehyde is a N-(6'-chlorohexyl)carbazole-3-carboxaldehyde.

* * * * *